United States Patent [19]

Akiba

[11] Patent Number: 5,109,202
[45] Date of Patent: Apr. 28, 1992

[54] CONDUCTIVE RESIN STRUCTURE FOR CONNECTING METAL CONDUCTORS

[76] Inventor: Juji Akiba, 1-27-202, 494 Shimo-Kayama, Hitaka-machi, Iruma-gun, Saitama, Japan

[21] Appl. No.: 383,110

[22] Filed: Jul. 20, 1989

[30] Foreign Application Priority Data

Aug. 11, 1988 [JP] Japan .............. 63-105378[U]

[51] Int. Cl.⁵ .................. G01R 27/22; G08B 21/00
[52] U.S. Cl. .................................. 324/693; 324/724; 340/605; 174/11 R
[58] Field of Search .............. 324/693, 698, 557, 718, 324/724; 340/604, 605; 73/40; 174/11 R; 200/61.04, 61.05

[56] References Cited

U.S. PATENT DOCUMENTS

| | | | |
|---|---|---|---|
| 2,742,541 | 4/1956 | Bunting | 200/61.06 |
| 3,486,037 | 12/1969 | Romano | 307/118 |
| 3,824,460 | 7/1974 | Gustafson | 340/604 X |
| 4,029,889 | 6/1977 | Mizuochi | 340/605 X |
| 4,319,232 | 3/1982 | Westphal et al. | 340/604 |
| 4,563,674 | 1/1986 | Kobayashi | 340/605 X |
| 4,570,477 | 2/1986 | Sugibuchi | 73/40.5 R |
| 4,677,371 | 6/1987 | Imaizumi | 324/52 |
| 4,677,373 | 6/1987 | Kobayashi et al. | 324/65 CR |
| 4,877,923 | 10/1989 | Sahakian | 174/11 R |
| 4,926,129 | 5/1990 | Wasley et al. | 174/11 R X |

Primary Examiner—Jack B. Harvey
Attorney, Agent, or Firm—Gary A. Samuels

[57] ABSTRACT

A structure for connecting metal conductors in an oil-leak detector having the conductors covered with porous polytetrafluoroethylene (PTFE) and the metal conductors connected by a band of carbon-filled porous PTFE. The conductors, the porous polytetrafluoroethylene and the band of porous polytetrafluoroethylene surrounded by a hydrocarbon-penetrable jacket.

3 Claims, 1 Drawing Sheet

CONDUCTIVE RESIN STRUCTURE FOR CONNECTING METAL CONDUCTORS

FIELD OF THE INVENTION

The invention relates to the field of connecting metal electrical conductors by a conductive resin.

BACKGROUND OF THE INVENTION

In recent years, electrically conductive resins have been developed and such conductive resins are increasingly used to make electrical connections between metal conductors, depending on the application involved and the location of use. For example, connecting structures of this type are employed in the detecting parts of oil leakage detection sensors which are used in order to check for oil leakage from oil tanks, piping in chemical plants, or aqueous or organic fluid carrying piplines.

Conductive resins such as carbon-filled polytetrafluoroethylene (PTFE) endowed with electrical conductivity by the admixture of powdered carbon in a PTFE insulation material, are used in the sensing parts of oil leakage detection sensors. PTFE resins have the property of repelling water while allowing the permeation of oil. In addition, carbon-filled PTFE resins have the property of showing a change in electrical resistance when permeated by oil. Oil leakage detecting sensors utilize this property of carbon-filled PTFE resins.

A conventional oil leakage detecting sensor has a pair of conductive metal lead wires which are installed so that they are separated from each other. In the detecting part of the sensor, these lead wires are electrically connected with each other by a resistor or connecting piece which consists of carbon-filled PTFE resin. This resistor is usually in the form of a band between the wires. The respective edges of the resistor are bonded to the circumferential surfaces of the lead wires by means of a conductive adhesive, with each edge covering approximately half of the circumferential surface of the corresponding lead wire. Furthermore, these lead wires and the resistor are covered by an insulating substrate which may comprise a PTFE resin.

The respective lead wires of the oil leakage detecting sensor are connected to a detection circuit, so that a closed circuit is formed by the lead wires, resistor, and detection circuit. When oil contacts the detecting part of the oil leakage detecting sensor, the oil permeates through the insulating substrate and penetrates into the resistor. As a result, the electrical resistance of the resistor changes, so that an accompanying electrical change occurs in the detection circuit. As a result, the leakage of oil can be detected.

In the above conventional connecting structure, different materials, such as the lead wires, which are made of metal, and a resistor, which is made of a resin material, are directly bonded by means of an adhesive. Accordingly, the bonding strength is weak, which may lead to improper or inconsistent contact, and in some cases to an interruption of electrical continuity owing to peeling of the bonded area. As a result, such conventional structures have lacked reliability.

Further, since the resistor is in contact with only about half of the circumferential surface of each of the lead wires, the area of contact is small, so that there is a great increase in electrical resistance in the connecting part. In the case of an oil leakage detecting sensor, such as described above, this leads to a drop in sensitivity.

BRIEF DESCRIPTION OF THE INVENTION

The present invention is designed in light of the above problems encountered in the prior art. The object of the present invention is to provide an electrical connecting structure for connecting metal conductors which makes it possible to achieve a strong mechanical connection and a good electrical connection. The present invention is an electrical connecting structure for connecting metal conductors, which is characterized by covering the entire circumferences of at least the connection areas of the metal conductors that are to be connected with a covering comprising a conductive resin. The coverings around the connection areas of the respective metal conductors are electrically connected with each other via a connecting piece which comprises a conductive resin which is joined to said coverings.

Since the entire circumferences of the connection areas of the metal conductors are covered by the covering, the joint between each metal conductor and the corresponding covering is secure despite the fact that the materials involved are different materials. Furthermore, the contact area is also large. Accordingly, a good electrical connection is obtained. Furthermore, since both the coverings and the connecting piece are made of a resin material, a mechanically sufficient joint strength can be obtained in the joining of said coverings and connecting piece. As a result, a connection is obtained which is also favorable in terms of electrical characteristics.

DETAILED DESCRIPTION OF THE INVENTION

Figure 1:
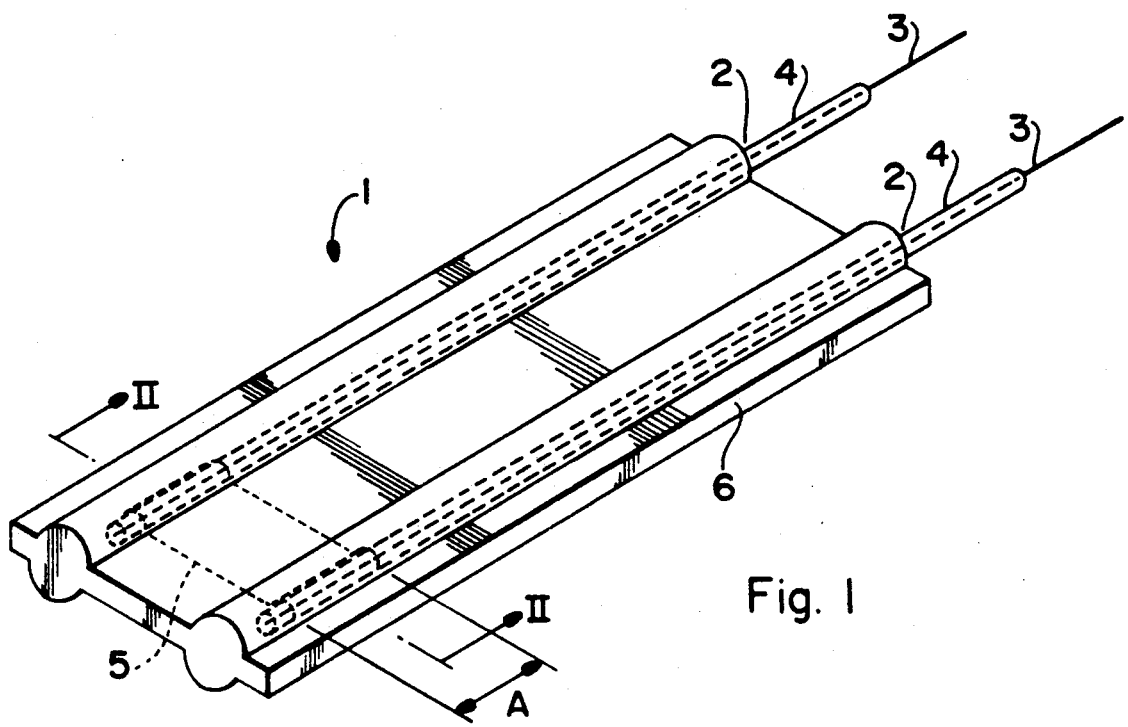
FIG. 1 is an oblique view of the detecting portion of an oil-leakage detector.
Figure 2:
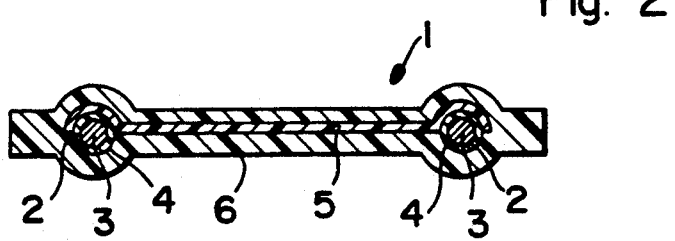
FIG. 2 is a cross-section of the detecting portion of the oil-leakage detector of FIG. 1 along line II—II.

With reference to FIGS. 1 and 2, a practical example of application of the present invention will be described. Furthermore, in this practical example of application, the electrical connecting structure for connecting metal conductors has the configuration found in the detecting part of an oil leakage detecting sensor.

FIG. 1 is an oblique view of the detecting part of the oil leakage detecting sensor 1. Oil leakage detecting sensor 1 has a pair of conductive carbon-filled PTFE resin-covered wires 2 which are installed so that they are separated from each other. Each wire 2 comprises a metal lead wire conductor 3 and a covering 4 which comprises a conductive carbon-filled PTFE resin and which covers the entire circumference of lead wire 3 in a tightly adhering state. Accordingly, the connection between lead wire 3 and covering 4 in each covered wire 2 is extremely strong mechanically. Also, since the area of contact is also large, this connection is also favorable from an electrical standpoint. Since the method used to cover lead wire 3 with covering 4 is the same as the method used generally to manufacture PTFE resin-covered wires, a description of this method is omitted here.

The tip portion of each of wires 2 forms a connection area A. In the connection areas A, the coverings 4 of the two wires 2 are electrically connected with each other via a resistor or connecting piece 5 which comprises conductive carbon-filled PTFE resin. Specifically, resistor 5 is a band-shaped part. Each of the edges of band-shaped part 5 is joined by thermal fusion to approximately half of the circumferential surface of one of the coverings 4 of wires 2. As is known, joints formed by thermal fusion are superior in terms of mechanical strength. Such a connection method is also extremely favorable from an electrical standpoint.

In this practical example of application, conductive carbon-filled PTFE resin-covered wires are utilized as described above. Accordingly, however, it would also be possible to cover only the connection area A of each lead wire 3 with covering 4.

Wires 2 and resistor 5 are covered by an insulating substrate comprising porous PTFE resin, so that one end of each of wires 2 is embedded in insulating substrate 6, while the other end of each wire 2 projects from insulating substrate 6. The projecting portions of wires 2 serve as terminals for connection to a detection circuit (not shown in the figures). Lead wires 3 are connected to the detection circuit by stripping away coverings 4 at the tips of the projecting portions of wires 2 as shown in FIG. 1. Further, after lead wires 3 have been connected to the detection circuit, wires 2 and naked lead wires 3 projecting from insulating substrate 6 may be covered by an insulation molded from an appropriate insulating material. In the oil leakage detecting sensor 1 as described above, the joints between the lead wires 3 and the coverings 4 and the joints between the coverings 4 and the resistor 5 are extremely strong mechanically. Accordingly, the joint areas tend not to be damaged even if oil leakage detecting sensor 1 is subjected to vibration or external forces. Further, these joints are also extremely favorable in terms of electrical characteristics. Accordingly, there are no problems of improper contact or interruption of electrical continuity as in the case of conventional devices. The electrical resistance of the connecting part can also be made smaller than is possible in the case of a conventional device, so that the sensitivity of oil leakage detecting sensor 1 is also improved.

The basic principle of oil leakage detection in this case is the same as that of a conventional oil leakage detecting sensor, i.e. the electrical resistance of resistor 5 and of coverings 4 in the connection areas A changes when the sensor is permeated by oil, and this change in electrical resistance is detected by the detection circuit.

This invention is not limited to the specific example of application described above; various other configurations may be used. For example, there is only one pair of lead wires 3 in the oil leakage detecting sensor described in the above example. It would also be possible to install two pairs of lead wires 3 or an even larger number of lead wires 3. Conductive resins which can be used in the present invention are not limited to conductive carbon-filled PTFE resins (conductive metal powders could be used), and this connecting structure may also be used in devices other than oil leakage detecting sensors. Other resins may be used, such as porous polyethylene, porous polypropylene, or porous rubber.

In the present invention, the entire circumferential surfaces of the connection areas of the metal conductors are covered by coverings. Accordingly, the invention has the following advantages; the joints between said metal conductors and coverings are extremely strong in mechanical terms; the area of contact is large, so that the joints provide favorable electrical characteristics to the detector. Further, since the insulative coverings and the connecting piece are both made of a resin material, a mechanically sufficient joint strength can be obtained in the joints between the coverings and the connecting piece. This also results in favorable electrical characteristics.

I claim:

1. Connected metal electrical conductors comprising:
   (a) at least two parallel metal electrical wire conductors each surrounded by a layer of electrically conducting resin comprising carbon-filled porous expanded polytetrafluoroethylene;
   (b) a band of electrically conducting resin comprising carbon-filled porous expanded polytetrafluoroethylene interconnecting said wire conductors and at least partially wrapping around and attaching to each said layer of conducting resin; and
   (c) a hydrocarbon-penetrable jacket surrounding said wire conductors, said conducting resin covering said conductors, and said conductive resin band.

2. A structure of claim 1, wherein said jacket comprises a porous hydrocarbon resin.

3. A structure of claim 2, wherein said porous hydrocarbon is selected from porous expanded polytetrafluoroethylene, porous polypropylene, porous polyethylene or porous rubber.

* * * * *